United States Patent
Hohlbein et al.

(10) Patent No.: US 8,550,736 B2
(45) Date of Patent: Oct. 8, 2013

(54) ORAL CARE IMPLEMENT

(75) Inventors: Douglas J. Hohlbein, Pennington, NJ (US); Chi Shing Wong, Warren, NJ (US)

(73) Assignee: Colgate-Palmolive Company, New York, NY (US)

( * ) Notice: Subject to any disclaimer, the term of this patent is extended or adjusted under 35 U.S.C. 154(b) by 372 days.

(21) Appl. No.: 12/717,206

(22) Filed: Mar. 4, 2010

(65) Prior Publication Data

US 2010/0160856 A1      Jun. 24, 2010

Related U.S. Application Data

(63) Continuation of application No. 11/852,621, filed on Sep. 10, 2007, which is a continuation of application No. 10/986,809, filed on Nov. 15, 2004, now Pat. No. 7,273,327, which is a continuation-in-part of application No. 10/869,922, filed on Jun. 18, 2004, now Pat. No. 7,143,462, and a continuation-in-part of application No. 10/601,106, filed on Jun. 20, 2003, now abandoned.

(60) Provisional application No. 60/600,701, filed on Aug. 11, 2004.

(51) Int. Cl.
*A61C 17/00* (2006.01)
*A61H 13/00* (2006.01)

(52) U.S. Cl.
USPC ......... 401/132; 15/104.93; 15/110; 15/167.1; 15/167.2; 601/139; 601/141; 606/161

(58) Field of Classification Search
USPC ........ 401/9, 132, 133, 268, 282; 15/110, 111, 15/167.1, 104.94, 104.93, 167.2; 606/161; 30/324; 601/139, 141
See application file for complete search history.

(56) References Cited

U.S. PATENT DOCUMENTS

| | | |
|---|---|---|
| D25,193 S | 2/1896 | Horton |
| 697,336 A | 4/1902 | Hagerty |
| 726,727 A | 4/1903 | Mills |
| 864,054 A | 8/1907 | Abrams |
| 1,002,468 A | 9/1911 | Strangman |
| 1,125,532 A | 1/1915 | Himmel |

(Continued)

FOREIGN PATENT DOCUMENTS

| | | |
|---|---|---|
| CH | 99738 | 6/1923 |
| CN | 99225704.2 | 11/1999 |

(Continued)

OTHER PUBLICATIONS

International Search Report and Written Opinion in International Application No. PCT/US05/028397 mailed Dec. 9, 2005.

*Primary Examiner* — David Walczak
*Assistant Examiner* — Joshua Wiljanen
(74) *Attorney, Agent, or Firm* — Ryan M. Flandro

(57) ABSTRACT

An oral care implement with a handle includes a head with a releasable material (e.g., an oral medicament) and a tissue cleaner for cleaning the soft tissues and removing odor-causing bacteria from the mouth. In one arrangement, the releasable material is disposed on the surface of the tissue cleaner. In one arrangement, the releasable material is disposed behind the tissue cleaner. In one arrangement, the releasable material is incorporated in the composition of the tissue cleaner.

23 Claims, 10 Drawing Sheets

(56) References Cited

U.S. PATENT DOCUMENTS

| | | |
|---|---|---|
| 1,128,139 A | 2/1915 | Hoffman |
| 1,142,698 A | 6/1915 | Crumbaugh |
| 1,153,409 A | 9/1915 | Wheeler |
| 1,191,556 A | 7/1916 | Blake |
| 1,251,250 A | 12/1917 | Libby |
| 1,268,544 A | 6/1918 | Cates |
| 1,470,710 A | 10/1923 | Davis |
| 1,495,675 A | 5/1924 | Colt |
| 1,598,224 A | 8/1926 | Van Sant |
| 1,658,706 A | 2/1928 | Carrott |
| 1,728,956 A | 9/1929 | Darmitzel |
| 1,741,143 A | 12/1929 | Chin |
| 1,749,632 A | 3/1930 | Ferris |
| 1,816,582 A | 7/1931 | Heron |
| 1,817,585 A | 8/1931 | Samuel |
| 1,860,924 A | 5/1932 | Cooke |
| 1,872,832 A | 8/1932 | Silverberg |
| 1,891,864 A | 12/1932 | Barrett |
| 1,892,068 A | 12/1932 | Matzler |
| 1,903,161 A | 3/1933 | Barkan |
| 1,965,009 A | 7/1934 | Stevens |
| 2,083,217 A | 7/1934 | Brothers et al. |
| 1,993,662 A | 3/1935 | Green |
| 1,993,763 A | 3/1935 | Touchstone |
| D99,352 S | 4/1936 | Grapp |
| 2,049,956 A | 8/1936 | Greenberg |
| 2,059,914 A | 11/1936 | Rosenberg |
| 2,075,681 A | 3/1937 | Welker |
| 2,079,728 A | 5/1937 | Arnold |
| 2,161,349 A | 6/1939 | Hadden |
| 2,186,005 A | 1/1940 | Casto |
| D122,815 S | 10/1940 | Crosby |
| 2,218,072 A | 10/1940 | Runnels |
| 2,233,936 A | 3/1941 | Campbell |
| 2,244,699 A | 6/1941 | Hosey |
| 2,253,210 A | 8/1941 | Psiharis |
| 2,253,910 A | 8/1941 | Luenz |
| 2,263,802 A | 11/1941 | Grusin |
| 2,405,029 A | 7/1946 | Gallanty et al. |
| 2,418,485 A | 4/1947 | Shipley |
| 2,491,274 A | 12/1949 | McNeill |
| 2,512,059 A | 6/1950 | Haeusser |
| 2,651,068 A | 11/1950 | Seko |
| 2,543,999 A | 3/1951 | Voss |
| D162,941 S | 4/1951 | Ehrman |
| 2,574,654 A | 11/1951 | Moore |
| 2,583,750 A | 1/1952 | Runnels |
| 2,642,604 A | 6/1953 | Ferrari |
| 2,708,762 A | 6/1953 | Kling et al. |
| 2,686,325 A | 8/1954 | Silver |
| 2,702,914 A | 3/1955 | Kittle et al. |
| 3,103,027 A | 9/1963 | Birch |
| 3,103,680 A | 9/1963 | Krichmar |
| 3,195,537 A | 7/1965 | Blasi |
| 3,254,356 A | 6/1966 | Yao et al. |
| 3,258,805 A | 7/1966 | Rossnan |
| 3,337,893 A | 8/1967 | Fine et al. |
| 3,509,874 A | 5/1970 | Stillman |
| 4,115,893 A | 9/1978 | Nakata et al. |
| 4,149,815 A | 4/1979 | Kawam |
| 4,176,980 A | 12/1979 | O'Neal et al. |
| 4,299,208 A | 11/1981 | Blanc |
| 4,328,604 A | 5/1982 | Adams |
| 4,356,585 A | 11/1982 | Protell et al. |
| 4,428,091 A | 1/1984 | Janssen |
| 4,432,114 A | 2/1984 | Goudsmit |
| 4,455,704 A | 6/1984 | Williams |
| 4,488,327 A | 12/1984 | Snider |
| 4,585,416 A | 4/1986 | DeNiro et al. |
| 4,610,043 A | 9/1986 | Vezjak |
| 4,628,564 A | 12/1986 | Youssef |
| D295,695 S | 5/1988 | Golzari |
| 4,827,551 A | 5/1989 | Maser et al. |
| 4,888,844 A | 12/1989 | Maggs |
| D309,528 S | 7/1990 | Valenti |
| 5,005,246 A | 4/1991 | Yen-Hui |
| 5,027,796 A | 7/1991 | Linzey |
| 5,032,082 A | 7/1991 | Herrera |
| 5,040,260 A * | 8/1991 | Michaels ..................... 15/167.1 |
| 5,061,106 A | 10/1991 | Kent |
| 5,133,971 A | 7/1992 | Copelan et al. |
| 5,213,428 A * | 5/1993 | Salman ........................... 401/7 |
| 5,217,475 A | 6/1993 | Kuber |
| 5,223,259 A | 6/1993 | Lackney |
| 5,226,197 A | 7/1993 | Nack et al. |
| H1228 H | 9/1993 | Doering |
| 5,242,235 A | 9/1993 | Li |
| 5,249,327 A | 10/1993 | Hing |
| 5,273,425 A | 12/1993 | Hoagland |
| 5,395,392 A | 3/1995 | Suhonen |
| 5,438,726 A | 8/1995 | Leite |
| 5,445,825 A | 8/1995 | Copelan et al. |
| 5,530,981 A | 7/1996 | Chen |
| 5,535,474 A | 7/1996 | Salazar |
| 5,584,690 A | 12/1996 | Maassarani |
| 5,604,951 A | 2/1997 | Shipp |
| 5,613,262 A | 3/1997 | Choy-Maldonado |
| 5,628,082 A | 5/1997 | Moskovich |
| 5,709,004 A | 1/1998 | Paduano et al. |
| 5,711,759 A | 1/1998 | Smith et al. |
| D391,769 S | 3/1998 | Kling et al. |
| 5,723,132 A * | 3/1998 | Tseng et al. .................. 424/401 |
| 5,735,011 A | 4/1998 | Asher |
| 5,735,864 A | 4/1998 | Heisinger, Jr. |
| 5,758,380 A | 6/1998 | Vrignaud |
| 5,766,193 A | 6/1998 | Millner |
| D396,288 S | 7/1998 | Samuel |
| 5,778,475 A | 7/1998 | Garcia |
| 5,779,654 A | 7/1998 | Foley et al. |
| D397,219 S | 8/1998 | Rangel et al. |
| 5,792,159 A | 8/1998 | Amin |
| 5,802,656 A | 9/1998 | Dawson et al. |
| 5,810,856 A | 9/1998 | Tveras |
| D399,349 S | 10/1998 | Barth |
| 5,817,114 A | 10/1998 | Anderson et al. |
| 5,845,358 A | 12/1998 | Woloch |
| D405,272 S | 2/1999 | Khlaj et al. |
| 5,875,510 A | 3/1999 | Lamond et al. |
| 5,896,614 A | 4/1999 | Flewitt |
| 5,913,346 A | 6/1999 | Narwani |
| 5,915,433 A | 6/1999 | Hybler |
| 5,928,254 A | 7/1999 | Jensen |
| 5,930,860 A | 8/1999 | Shipp |
| 5,938,673 A | 8/1999 | DePierro et al. |
| 5,951,578 A | 9/1999 | Jensen |
| 5,955,099 A | 9/1999 | White |
| 5,957,942 A | 9/1999 | Yudelman |
| 5,967,152 A | 10/1999 | Rimkus |
| 5,980,541 A | 11/1999 | Tenzer |
| 5,980,542 A | 11/1999 | Saldivar |
| 5,984,935 A | 11/1999 | Welt et al. |
| 6,015,293 A | 1/2000 | Rimkus |
| 6,032,315 A | 3/2000 | Liebel |
| 6,041,467 A | 3/2000 | Roberts et al. |
| D422,413 S | 4/2000 | Goldinger et al. |
| D423,785 S | 5/2000 | Karallis |
| D423,786 S | 5/2000 | Zelinski |
| D424,809 S | 5/2000 | Bernard |
| 6,066,162 A | 5/2000 | Hudson |
| 6,085,379 A | 7/2000 | Stafford |
| 6,105,191 A | 8/2000 | Chen et al. |
| 6,105,587 A | 8/2000 | Dunn |
| 6,119,296 A | 9/2000 | Noe et al. |
| 6,126,678 A | 10/2000 | Aaltonen et al. |
| 6,131,228 A | 10/2000 | Chen et al. |
| 6,159,492 A | 12/2000 | Manzone et al. |
| 6,165,495 A | 12/2000 | Blankenship |
| 6,171,323 B1 | 1/2001 | Potti et al. |
| 6,254,390 B1 | 7/2001 | Wagner |
| D447,238 S | 8/2001 | Tang |
| 6,289,545 B1 | 9/2001 | Molster |
| 6,311,358 B1 | 11/2001 | Soewtewey et al. |
| 6,311,360 B1 * | 11/2001 | Lanvers ........................ 15/191.1 |
| 6,322,573 B1 | 11/2001 | Murayama |

(56) References Cited

U.S. PATENT DOCUMENTS

| | | | |
|---|---|---|---|
| 6,352,545 | B1 | 3/2002 | Wagner |
| 6,383,202 | B1 | 5/2002 | Rosenblood |
| 6,402,768 | B1 | 6/2002 | Liebel |
| 6,421,867 | B1 | 7/2002 | Weihrauch |
| D461,959 | S | 8/2002 | Chan et al. |
| 6,446,295 | B1 | 9/2002 | Calabrese |
| 6,463,619 | B2 | 10/2002 | Gavney, Jr. |
| D465,847 | S | 11/2002 | Jacobs |
| 6,496,999 | B1 | 12/2002 | Gleason et al. |
| D471,276 | S | 3/2003 | Potti |
| 6,546,586 | B2 | 4/2003 | Cho |
| 6,602,013 | B2 | 8/2003 | Clark |
| 6,625,839 | B2 | 9/2003 | Fischer |
| 6,647,581 | B1 | 11/2003 | Persad et al. |
| 6,672,316 | B1 | 1/2004 | Weihrauch |
| 6,729,789 | B2 | 5/2004 | Gordon |
| 6,769,828 | B2 | 8/2004 | Clark |
| 7,036,179 | B1 | 5/2006 | Weihrauch |
| 2001/0023516 | A1 | 9/2001 | Driesen et al. |
| 2001/0039689 | A1 | 11/2001 | Gavney, Jr. |
| 2001/0041903 | A1 | 11/2001 | Richard |
| 2002/0004964 | A1 | 1/2002 | Luchino et al. |
| 2002/0019645 | A1 | 2/2002 | Fischer et al. |
| 2002/0108194 | A1 | 8/2002 | Carlucci et al. |
| 2002/0124337 | A1 | 9/2002 | Calabrese et al. |
| 2002/0138926 | A1 | 10/2002 | Brown, Jr. et al. |
| 2002/0138928 | A1 | 10/2002 | Calabrese |
| 2002/0198412 | A1 | 12/2002 | Green et al. |
| 2003/0075731 | A1 | 4/2003 | Chen et al. |
| 2003/0115699 | A1 | 6/2003 | Wagstaff |
| 2003/0163149 | A1 | 8/2003 | Heisinger, Jr. |
| 2003/0167582 | A1 | 9/2003 | Fischer et al. |
| 2003/0216762 | A1 | 11/2003 | Levit |
| 2004/0152031 | A1 | 8/2004 | Takahashi |
| 2004/0255416 | A1 | 12/2004 | Hohlbein |

FOREIGN PATENT DOCUMENTS

| | | | |
|---|---|---|---|
| DE | 857 128 | | 11/1952 |
| DE | 29 30 459 | | 2/1981 |
| DE | 31 14 507 | A1 | 3/1983 |
| DE | 36 39 424 | A1 | 6/1988 |
| EP | 0875169 | A | 4/1998 |
| EP | 1350442 | | 10/2003 |
| FR | 537979 | | 6/1922 |
| FR | 2594307 | A1 | 4/1987 |
| GB | 17643 | | 4/1912 |
| GB | 495982 | | 11/1938 |
| GB | 1026738 | A * | 4/1966 |
| GB | 2351015 | | 12/2000 |
| GB | 2391462 | | 2/2004 |
| JP | 2000-308522 | | 11/2000 |
| JP | 2001-314232 | | 11/2001 |
| JP | 2002-142867 | | 5/2002 |
| RU | 1708283 | | 1/1992 |
| RU | 2113155 | | 6/1998 |
| SU | 1708283 | | 1/1992 |
| WO | WO 98/09573 | | 3/1998 |
| WO | WO 99/49754 | A1 | 10/1999 |
| WO | WO 00/64307 | | 2/2000 |
| WO | WO 01/17433 | A1 | 3/2001 |
| WO | WO 01/26564 | | 4/2001 |
| WO | WO 01/34042 | | 5/2001 |
| WO | WO 01/39674 | | 6/2001 |
| WO | WO 01/45573 | A1 | 6/2001 |
| WO | WO 01/80686 | A2 | 11/2001 |
| WO | WO 02/071967 | A2 | 9/2002 |
| WO | WO 2004/021914 | | 3/2004 |
| WO | WO 2004/026162 | | 4/2004 |

* cited by examiner

ORAL CARE IMPLEMENT

CROSS-REFERENCE TO RELATED APPLICATIONS

This application is a continuation of U.S. application Ser. No. 11/852,621, filed Sep. 10, 2007, which is a continuation of U.S. application Ser. No. 10/986,809, filed Nov. 15, 2004, now U.S. Pat. No. 7,273,327, which is a continuation in-part of U.S. patent application Ser. No. 10/869,922 filed Jun. 18, 2004, now U.S. Pat. No. 7,143,462, and a continuation in-part of U.S. patent application Ser. No. 10/601,106 filed Jun. 20, 2003, now abandoned, and claims the benefit of U.S. Provisional Application No. 60/600,701, filed Aug. 11, 2004; the entirety of which applications are expressly incorporated herein by reference.

FIELD

The present invention pertains to an oral care implement with a tissue cleaner and a releasable material for engaging tissue of the mouth.

BACKGROUND

According to the American Dental Association, a major source of bad breath in healthy people is microbial deposits on the tongue, where a bacterial coating harbors organisms and debris that contribute to bad breath. Tissue in the mouth, and especially the tongue, is a haven for the growth of microorganisms. The papillary nature of the tongue surface creates a unique ecological site that provides an extremely large surface area, favoring the accumulation of oral bacteria. Anaerobic flora and bacteria residing on the tongue and other soft tissues in the mouth play an important role in the development of chronic bad breath commonly called halitosis. In general, the bacteria produce volatile sulfur compounds (VSC). If there is enough buildup of the sulfur compounds, the result can lead to bad breath or oral malodor.

While tongue scrapers have been used in the past, they have generally not been effective, easy to use, or socially acceptable for use in a public setting. Further, many of these scrapers cannot easily be used to cleanse other tissue within the mouth. Notwithstanding the benefits to be gained by cleaning the tissue in the mouth, many users avoid the use of such cleaners due to a lack of comfort and/or ease of use.

In addition, it has not been convenient or socially acceptable for users to clean their tongues and other soft tissue in the mouth in public settings, on the go or, away from home.

Hence, there is a need for an oral care implement with a tongue cleaner that provides effective removal of the tongue bacteria and other debris, maintains comfort to the user, provides a substance to treat tissues of the mouth, is easy to use, and is socially acceptable and convenient in public settings or on the go. There is also a need for an oral implement which combines the cleaning effects of a tissue cleaner and medicament.

BRIEF SUMMARY OF THE INVENTION

The invention pertains to an oral care implement includes a tissue cleaner which provides improved cleaning and effective removal of bacteria and microdebris disposed on the oral tissue surfaces.

In one aspect of the invention, a releasable material is supported by an insoluble tissue cleaner that includes at least one tissue engaging element for cleaning tissue surfaces in the mouth. The tissue engaging element(s) may be rubbed along the oral tissue to remove bacteria and debris while a chemical of the releasable material is released into the mouth of a user. In one preferred embodiment, the releasable material is provided as an antiseptic and/or breath freshener for enhanced cleaning and freshening of the mouth.

In another aspect of the invention, the tissue cleaner is composed of an elastomeric material. In one preferred embodiment, the tissue cleaner is formed as an elastomeric molded element provided with a plurality of exterior nubs. The tissue cleaner may include an interior or an exterior supporting surface of an oral medicament.

In another aspect of the invention, the oral care implement includes a cavity to hold an oral medicament for ease of releasing the medicament into the mouth.

In another aspect of the invention, the oral care implement resembles a lollipop for convenience, ease of use and social acceptance. In one preferred embodiment, the tongue cleaner and/or medicament has a disk shape and is mounted on the end of a stick.

In another aspect of the invention, a chemical is incorporated into the material of a tissue cleaner. In one preferred embodiment, the chemical is released from the tissue cleaner for creating a sensory response to the tissues inside of the mouth of a user.

BRIEF DESCRIPTION OF THE DRAWINGS

A more complete understanding of the present invention and the advantages thereof may be acquired by referring to the following description in consideration of the accompanying drawings, in which like reference numbers indicate like features, and wherein.

DETAILED DESCRIPTION OF THE INVENTION

Figure 1:
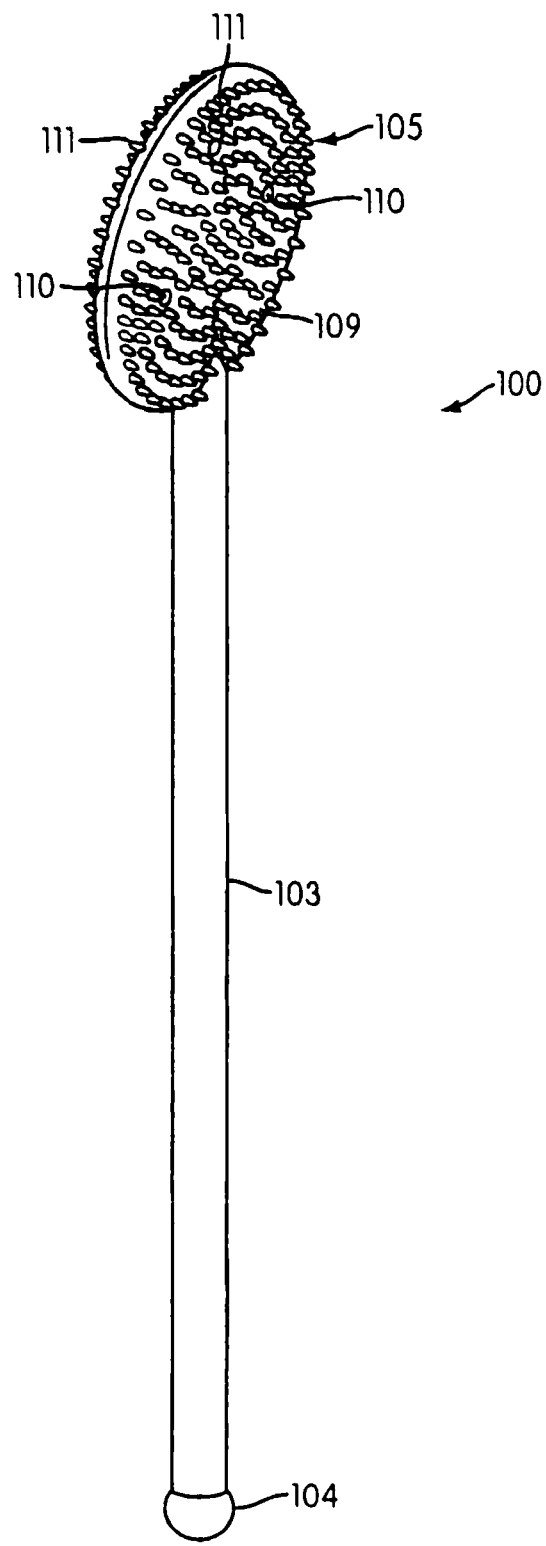
FIG. 1 is a perspective view of a first oral care implement according to one or more aspects of the invention.

FIGS. 1-5 illustrate an oral care implement 100 with a grip portion or handle 103 and a head 105 for reducing oral malodor and cleaning the tissue in the mouth, such as the tongue, interior surfaces of the cheeks, lips or the gums. Among other features, oral care implement 100 enables convenient on-the-go or away from home use to clean the tissues of the mouth. Head 105 includes both a tissue cleaner 109 and a releasable material 107. Handle 103 is provided for the user to readily grip and manipulate the oral implement 100. While the handle 103 is generally cylindrical, it may have many different shapes and constructions. Though the head preferably has a rounded or bulbous construction relative to the handle, it could in some constructions simply be a continuous extension of the handle.

As can be appreciated, oral care implement 100 preferably resembles a lollipop in its construction for convenience, compact size, ease of use, and social acceptance. With this construction, users can readily carry and use the implement without drawing attention to themselves or feeling self-conscious about cleansing their mouths, particularly if they are in a public place. Moreover, this preferred form of the invention can be easily transported for use while on the go by many active users. Such ease and convenience is a significant benefit for those wishing to cleanse their mouths before interactions with others, such as meetings at work, social engagements, etc. particularly for those on the go, between activities, away from home, or in a public setting.

Figure 2:
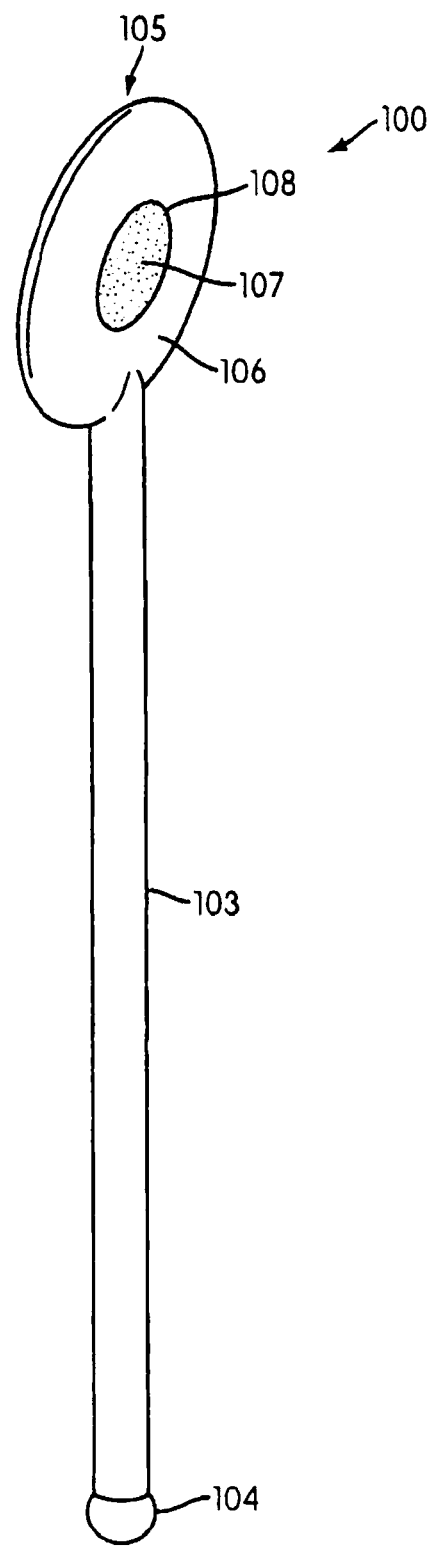
FIG. 2 is a perspective view of the oral care implement of FIG. 1 with the tissue cleaner omitted to show the Support and releasable material therein.
Figure 5:
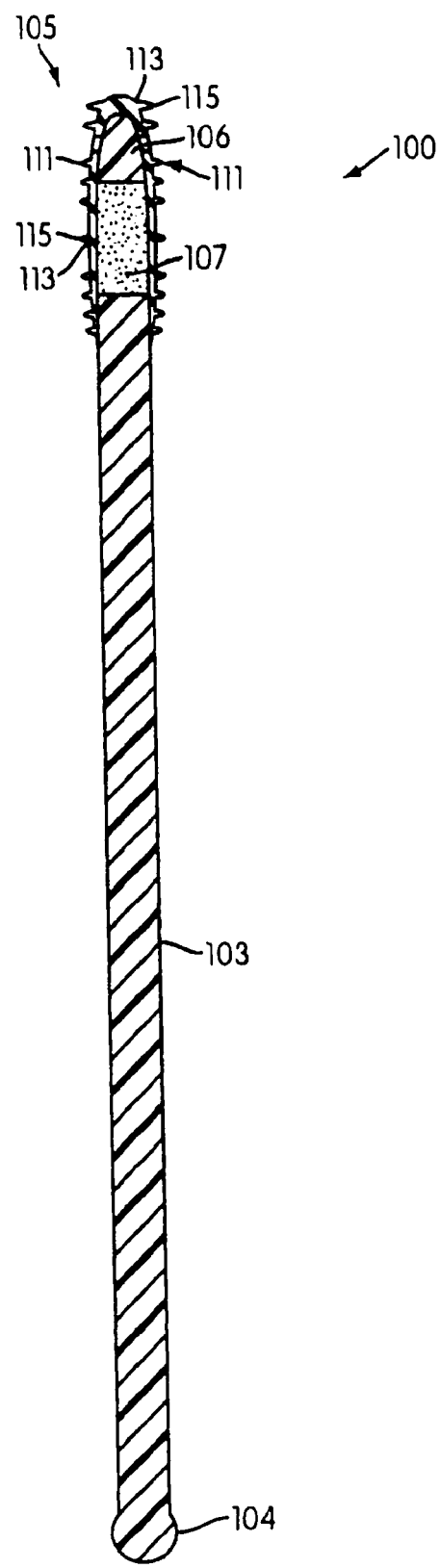
FIG. 5 is a section view of the oral care implement of FIG. 1 taken along line 5-5 in FIG. 3.

Referring to FIGS. 2 and 5, the releasable material 107 can be any suitable biocompatible medication or chemical for oral use. The releasable material 107 can be provided in a suitable shape in a tablet form for oral use or any other suitable form. The releasable material 107 may be released to the inside of the mouth, lips, or cheeks by way of several methods, including but not limited to abrasion, a temperature change, a change in pH or dissolution.

Preferably, the releasable material is a soluble breath freshening agent which dissolves in an oral fluid, such as saliva. The breath freshening agent may be an anti-bacterial substance used to treat anaerobic flora and bacteria residing on the tongue or other soft tissues of the mouth. One example of a breath freshening agent which may be used is triclosan.

In other constructions, the releasable material 107 can comprise a chemical substance which imparts other benefits. For example, a chemical substance (e.g., a sensate) can be used to provide a biochemical sensory response to the inside tissue of the mouth and/or lips of a user. As one example, a chemical substance known as capsiason can be used to provide a tingle, a warm massage, or a soothing sensation to a user. In another example, spillanthol can be used to provide a residual tingle sensation as well as breath freshening benefits. In another example, chamomile and lavender can be used to provide stress relief and relaxation benefits to the user. In yet another example, a flavoring can be used to enhance the user's enjoyment during cleansing of the mouth.

In yet other constructions, the releasable material 107 can comprise a chemical or medicament for oral benefits. For example, HUMPHRIES 3 or benzocaine can be used for pain relief. In another example, zo-caine type of medicines can be used as an appetite suppressant for weight loss treatment. In yet another example, the releasable material can be aspirin and the like. In an alternative construction, the releasable material may be a health supplement, such as a vitamin or mineral. Nevertheless, a wide variety of other chemicals which provide a medicinal or sensory response can be used with the oral care implement. Also, depending on the chemicals, a plurality of chemicals may be combined in tablets or the like of releasable material for multiple benefits.

Tissue cleaner 109 includes at least one tissue engaging element for cleansing oral tissue and means for retaining the releasable material 107. As shown in the arrangement of FIGS. 1-5, tissue cleaner 109 is formed as a bulbous or disk-like element composed of a soft pliable elastomeric material for comfortable cleaning and effective removal of bacteria and debris disposed on tissue in the mouth, such as the tongue, inner surfaces of the cheeks, gums, and lips. The tissue cleaner 109 also provides effective massaging, stimulation and removal of epithelial cells from the oral tissue.

The elastomeric material of tissue cleaner 109 may be any biocompatible resilient material suitable for uses in an oral hygiene apparatus. To provide optimum comfort as well as cleaning benefits, the elastomeric material preferably has a hardness property in the range of A8 to A25 Shore hardness. As an example, one preferred elastomeric material is styrene-ethylene/butylene-styrene block copolymer (SEBS) manufactured by GLS Corporation. Nevertheless, SEBS material from other manufacturers or other materials within and outside the noted hardness range could be used.

Tissue cleaner 109 is preferably configured with a multiplicity of tissue engaging elements 111 (FIGS. 1 and 3-5), which in the preferred construction are formed as nubs, and which will be described hereinafter for purposes of simplicity as "nubs." As used herein a "nub" is generally meant to include a column-like protrusion (without limitation to the cross-sectional shape of the protrusion) which is upstanding from a base surface. In a general sense, the nub, in the preferred construction, has a height that is greater than the width at the base of the nub (as measured in the longest direction). Nevertheless, nubs could include projections wherein the widths and heights are roughly the same or wherein the heights are somewhat smaller than the base widths. However, in some circumstances (e.g., where the nub tapers to a tip or includes a base portion that narrows to a smaller projection), the base width can be substantially larger than the height.

Nubs 111 enable mechanical removal of microflora and other debris from the teeth, tongue and other soft tissue surfaces within the mouth. The tongue, in particular, is prone to develop bacterial coatings that are known to harbor organisms and debris that can contribute to bad breath. This microflora can be found in the recesses between the papillae on most of the tongue's upper surface as well as along other soft tissue surfaces in the mouth. When engaged or otherwise rubbed against a tongue surface, for example, nubs 111 provide for gentle engagement with the soft tissue while reaching downward into the recesses of adjacent papillae of the tongue. The elastomeric construction of tissue cleaner 109 also enables the head 105 to follow the natural contours of the oral tissue surfaces, such as the tongue, cheeks, lips, and gums of a user. Moreover the nubs 111 are preferably soft so as to flex as needed to traverse and clean the tissue surfaces in the mouth. In the preferred construction, nubs 111 are able to flex and bend from their respective vertical axes as lateral pressure is applied during use. This flexing enhances the comfort and cleaning of the soft tissue surfaces.

Figure 4:
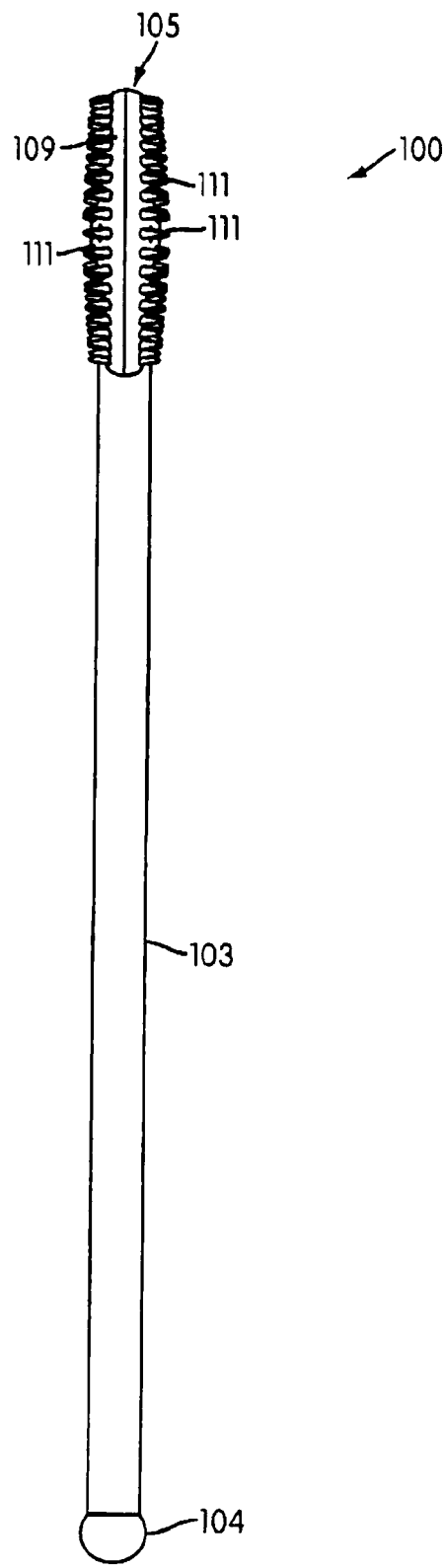
FIG. 4 is a side view of the oral care implement of FIG. 1.

As seen in FIGS. 1 and 4-5, in one preferred arrangement of tissue cleaner 109, nubs 111 are preferably conically or substantially conically shaped, although other configurations are contemplated. As used herein, "conically shaped" or "conical" is preferably meant to include true cones, frusto-conically shaped elements, and other shapes that taper to a narrow end and thereby resemble a cone irrespective of whether they are uniform, continuous in their taper, or have rounded cross-sections. With reference to FIG. 5, the base portion 113 of the conically shaped tissue engaging elements 111 is larger than the corresponding tip portion 115 and has a wider cross-sectional area to provide effective shear strength to withstand the movement of the tissue cleaner 109 along a soft tissue surface. The preferably smaller width or diameter of the tip portion 115 in conjunction with the length of the conically shaped nub 111 enable the nubs to sweep into the recesses of the tongue and other surfaces to clean the microbial deposits and other debris from the soft tissue surfaces. Further this construction effectively enables the releasable material to enter the recesses of the adjacent papillae of the tongue for oral care treatment.

In a preferred construction, the thickness or width of the base of the nub is 0.64 mm, and preferably within the range from about 0.51 mm to about 2.00 mm. Tip 115 of the nub is 0.127 mm in width and preferably within a range from about 0.0.10 mm to about 0.75 mm for optimal penetration between the recesses of papillae of a user's tongue. The length or height of the nubs 111 as measured from base surface 113 to tip 115, is preferably 0.91 mm and preferably within range from about 0.5 mm to about 2.5 mm, and most preferably range between 0.75 mm to 1.5 mm. It should be recognized that the foregoing dimensions are provided to generally correspond to the typical anatomy of a human tongue which does not deviate significantly from the norm. Nevertheless, nubs of other sizes and shapes outside the given ranges can be used.

Figure 3:
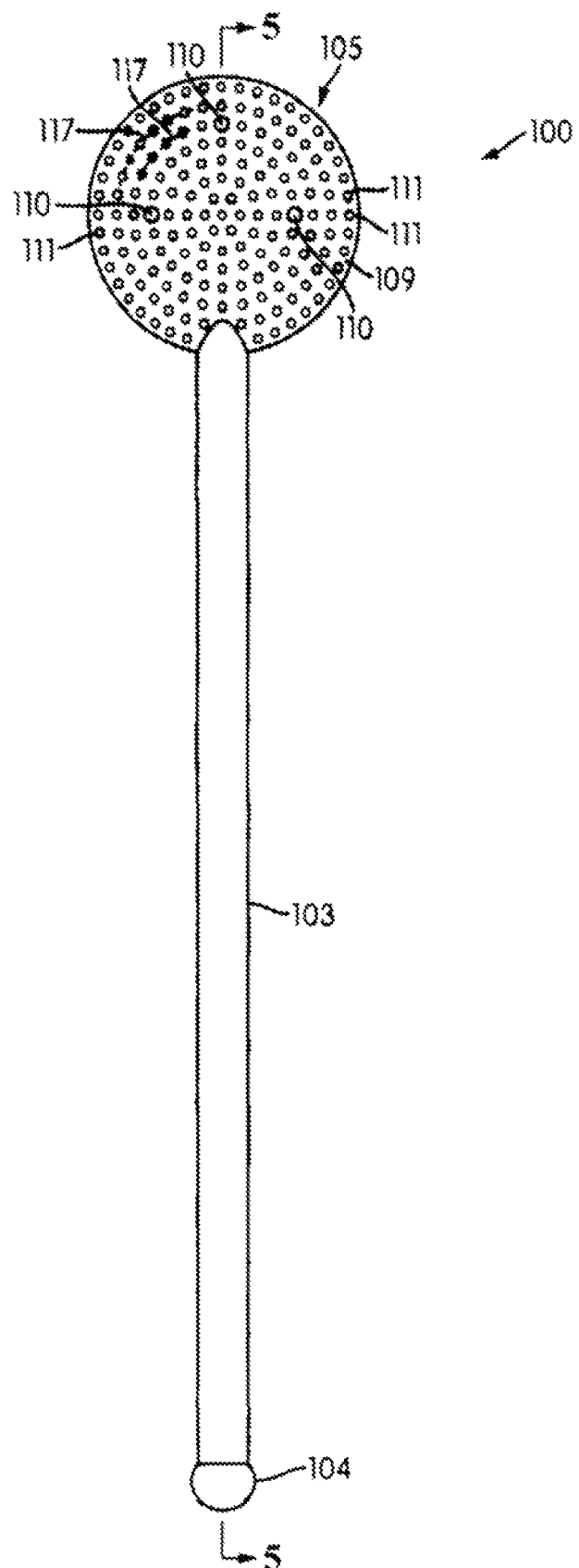
FIG. 3 is a front view of the oral care implement of FIG. 1.

As seen in FIG. 3, nubs 111 are preferably disposed in concentric rings, rows or loops 117 at spaced radial distances from the center of the head 105. This configuration encourages natural small circular motions on the tongue surface and other soft tissues to effectively clean the tissue and promote a user's salivary flow to release the releasable material 107 into the mouth. Further, the motion of the head and nub construction helps force the releasable material 107 into the adjacent papillae of the tongue. In one preferred construction, nubs 111 on adjacent loops 117 may be radially aligned. For example, adjacent loops 117 have nubs 111 that are directly behind each other. A first nub is said herein to be "directly behind" a second nub when it is located within the lateral bounds of the second nub extending in a radial direction. In an alternative arrangement, the adjacent loops 117 can be in a staggered arrangement where the nubs are not directly radially behind another nub. These configurations enable improved cleaning of the soft tissue surfaces by facilitating the removal of microflora and other debris and providing the oral medicament especially in the recesses of adjacent papillae of the tongue. Nonetheless, the nubs could be arranged randomly or in a myriad of different ordered patterns.

While a description of a preferred embodiment of the tissue cleaner has been discussed, it should be understood that benefits of the invention can still be obtained with a wide variety of tissue cleaner constructions. For example, the tissue engaging elements may be in forms other than nubs, such as, for example, ridges or hemispheres. The tissue engaging elements may be formed on one side, a part of a side or sides, both sides, or the entire periphery of the tissue cleaner. Finally, the tissue cleaner may be formed of a non-elastomeric material or a combination of different materials. In an alternative embodiment, the opposing end 104 of the handle opposite the head 105 may be used for oral hygiene benefits. For example, the end 104 may include a small toothbrush, a flossing bow, or a toothpick.

In the arrangement of oral care implement 100 shown in FIG. 2, the head 105 preferably includes a base 106 with an aperture or cavity 108 of tissue cleaner 109 (FIG. 1) to hold and retain the unreleased form of the releasable material 107. The disk shaped base 106 provides a surface for over-molding of the tissue cleaner 109. In a preferred construction, the releasable material 107 is also covered by the elastomeric surface of the tissue cleaner 109 (see FIG. 5). Base 106 is preferably formed of a hard or flexible plastic, but could be Formed of an elastomer or other materials. Further, the base could be a unitary portion of the elastomeric material forming the tissue cleaner 109.

As shown in FIGS. 1 and 3, the tissue cleaner 109 includes holes 110 in the elastomer surface which enable the releasable material 107 to dissolve and release the chemical into the mouth of a user. As an alternative, the releasable material may be a fluid that is encapsulated in an outer layer that dissolves or is broken by the user's teeth to release the chemical. In either construction, effective cleaning of the tissue surfaces in the mouth may be obtained though the combined use of the tissue cleaner 109 mechanically scrubbing the tissue surfaces and the beneficial effects of applying and breath freshener/antiseptic around the oral cavity. Also, by enclosing the releasable material within the tissue cleaner, most of the surface area of the tissue cleaner 109 is provided for cleaning performance.

Figure 6:
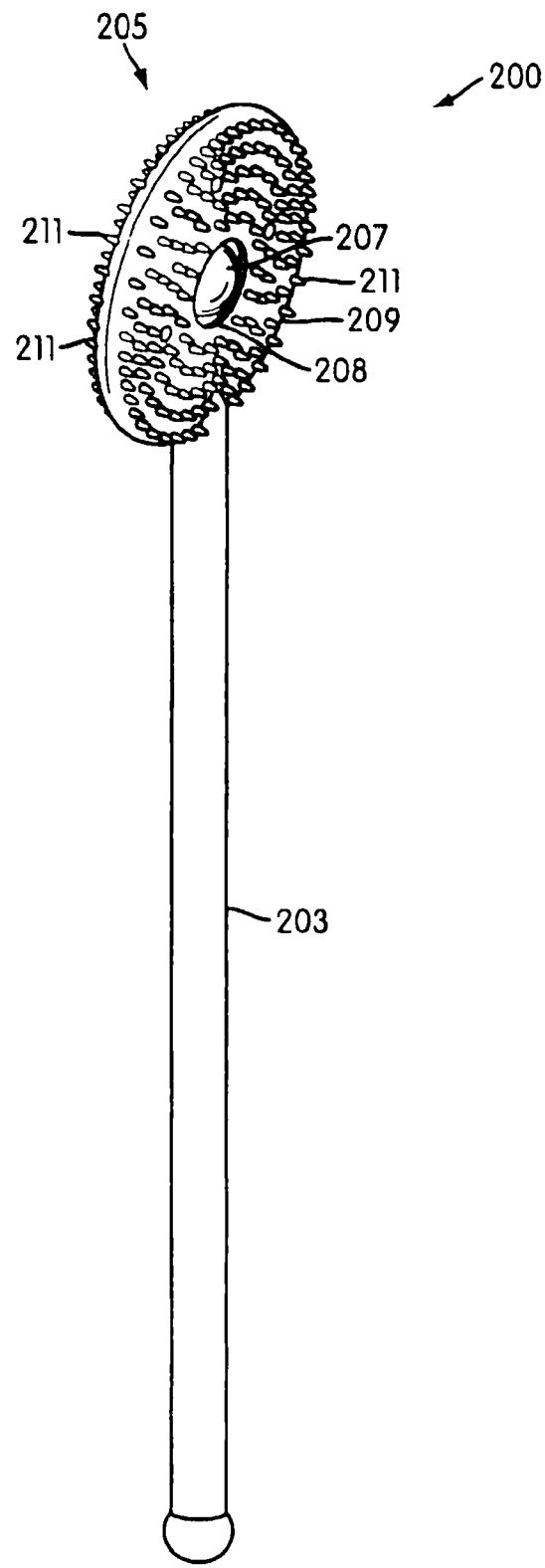
FIG. 6 is a perspective view of a second oral care implement according to one or more aspects of the invention.
Figure 7:
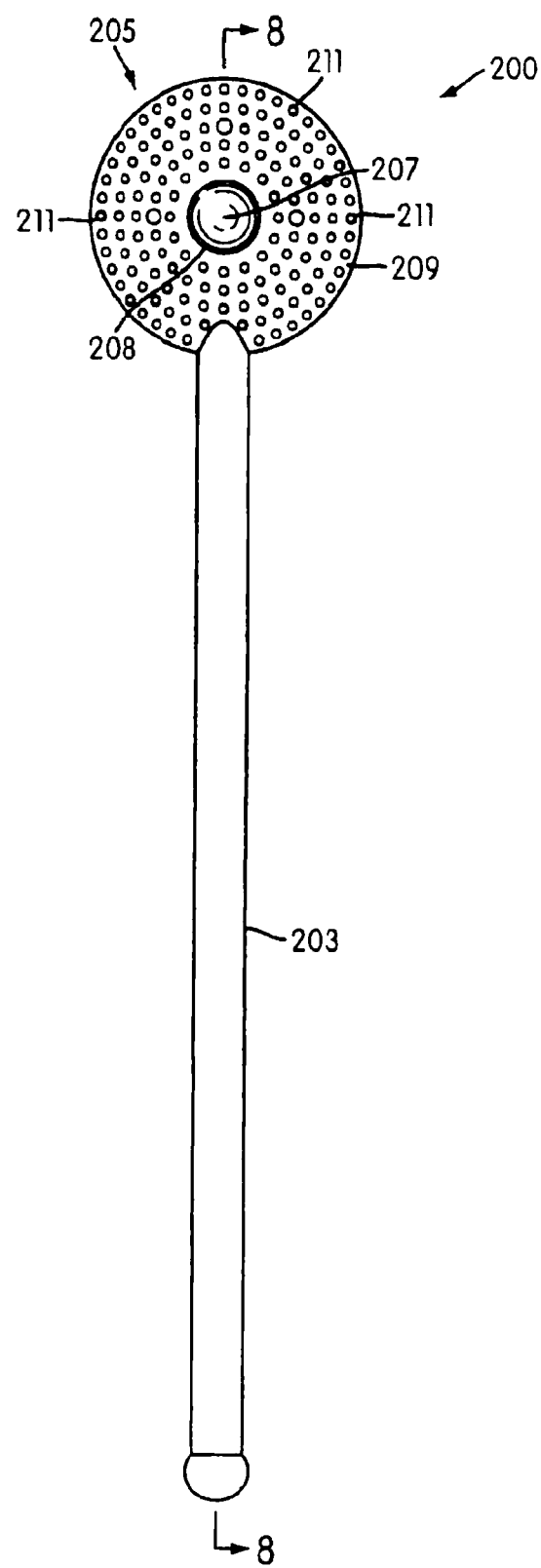
FIG. 7 is a front view of the oral care implement of FIG. 6.
Figure 8:
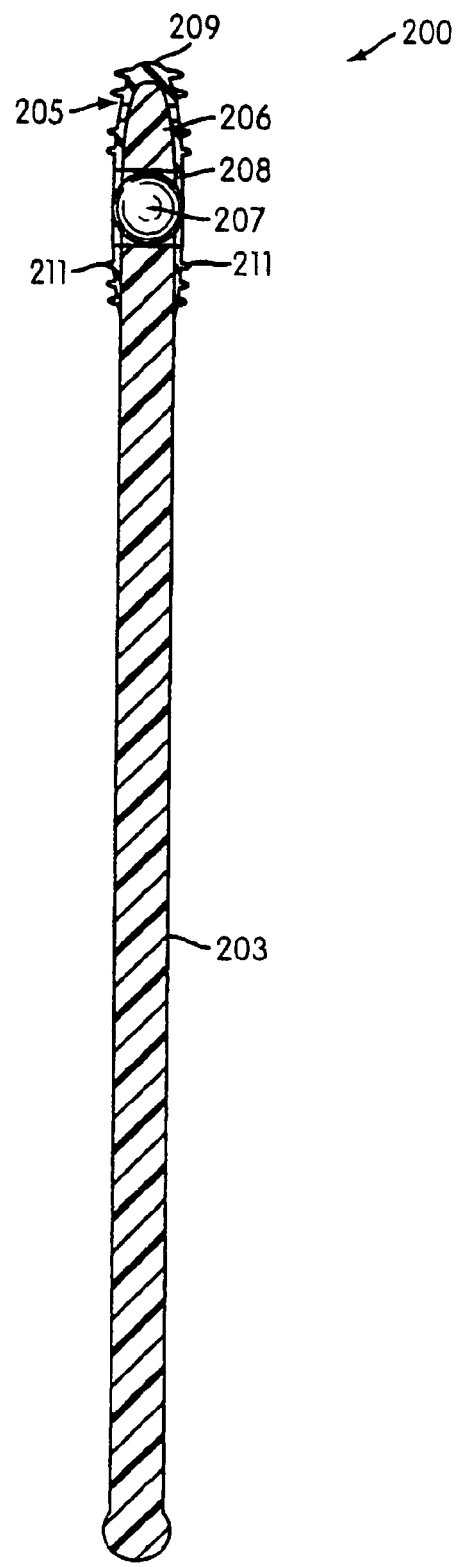
FIG. 8 is a section view of the oral care implement of FIG. 6 taken along line 8-8 in FIG. 7.

FIGS. 6-8 illustrate an alternative embodiment of an oral care implement 200 with a handle 203 and a head 205 for reducing oral malodor and cleaning the soft tissue in the mouth. The embodiment of oral care implement 200 is similar in construction to the oral care implement 100 of FIGS. 1-5, except that a tissue cleaner 209 has an opening 208 visibly exposing a releasable material 207 for use. While opposing sides of the releasable material 207 is exposed in the head 205, only one side of the material 207 may be exposed. Tissue cleaner 209 includes tissue engaging elements 211 similar in construction to nubs 111 as tissue cleaner 109. In a preferred construction, the releasable material 207 in the form of a liquid breath freshener (or other material) is provided as a small bead, tablet, or the like, which is supported in the interior of the head 205. The releasable material 207 may be a solid dissolvable bead or a liquid encapsulated in a dissolvable or breakable outer cover (e.g., a container). In the most preferred arrangement, the releasable material may be disposed in the center of the head 205. As noted, releasable material 207 may be broken by the teeth of a user or dissolved by the saliva to release a liquid breath freshener and/or antiseptic in the mouth. Nevertheless, other types of the releasable materials may be used. In one arrangement, the user may replace the releasable material 207 in the elastomeric tissue cleaner 209 for multiple uses of the oral care implement 200. In such an embodiment, the releasable material 207 can be pressed into the opening 208 for a snug fit and retained by frictional forces or held in another mechanical manner.

Figure 9:
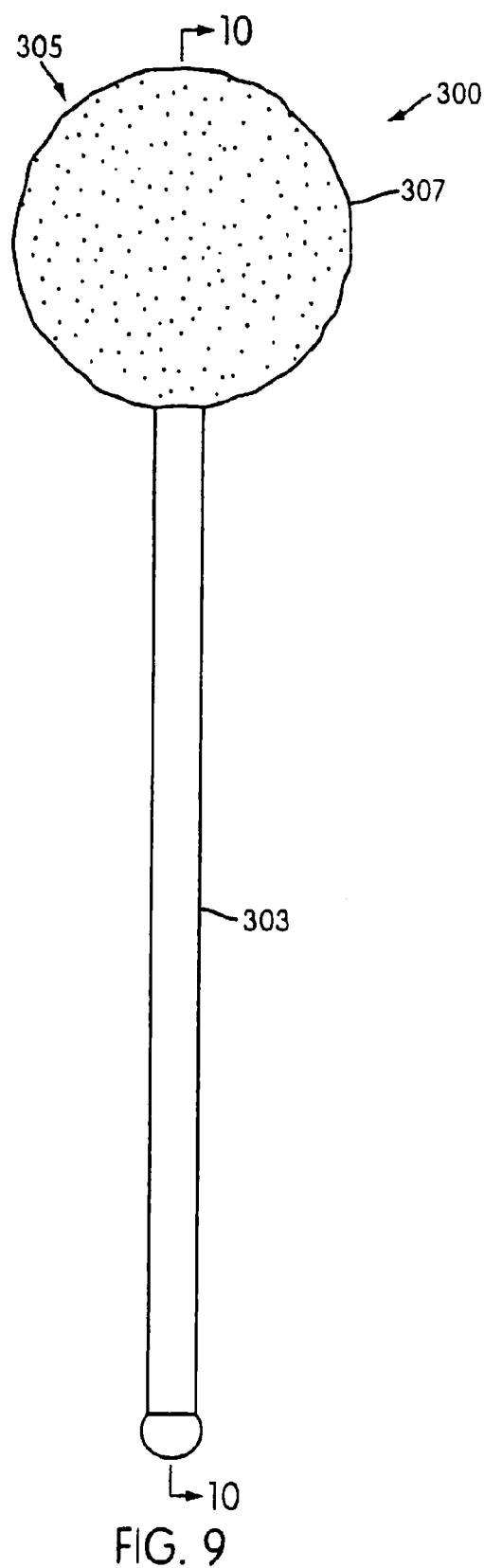
FIG. 9 is a front view of a third oral care implement according to one or more aspects of the invention.
Figure 10:
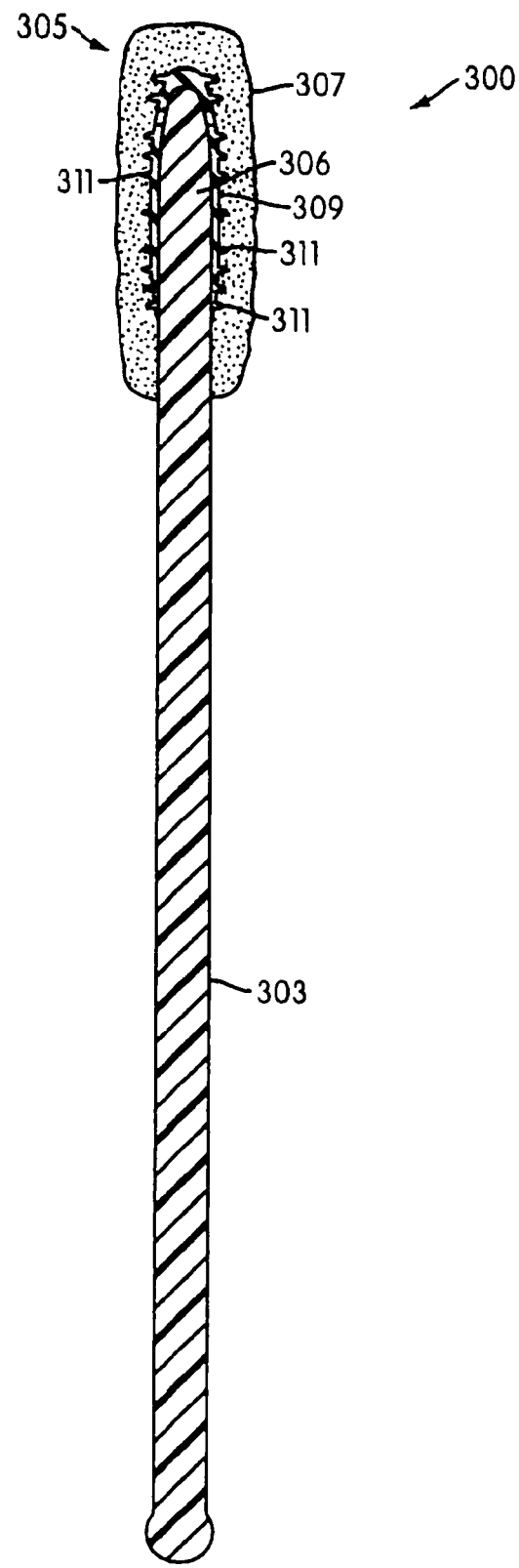
FIG. 10 is a section view of the oral care implement of FIG. 9 taken along line 10-10 in FIG. 9.

FIGS. 9-10 illustrate an alternative embodiment of an oral care implement 300 with a handle 303 and a head 305 for reducing oral malodor and cleaning the soft tissue in the mouth. The embodiment of oral care implement 300 is similar in construction to the oral care implement 100 of FIGS. 1-5, except that a tissue cleaner 309 supports the releasable material on its exterior. For example, the tissue cleaner is covered, coated, or otherwise, encased within a releasable material 307 (see FIG. 10). While a breath freshener coating is preferred, the coating also could be a medicine, a sensate or combination of materials. Tissue cleaner 309 includes tissue engaging elements 311 similar in construction as tissue cleaner 109. There are many forms of the releasable material 307 which can be used on the tissue cleaner 309. In a preferred construction, the material 307 may be a confectionary applied to the tissue cleaner 309 by a casting or dipping process, although other methods could be used. In this construction, the material 307 can be dissolved in the mouth revealing elements 311 to treat the soft tissues then the user may clean debris therefrom with the elements 311.

In an alternative arrangement of the oral care implement 300, the releasable material may be provided in solution, emulsion or microencapsulation form, then deposited or applied to form a continuous or semi-continuous coating on the surface of the tissue cleaner 309. The deposited solution, emulsion or microencapsulation may be then be air-dried, heat assisted dried, heat assisted cured, catalyst assisted cured, or ultra-violet (UV) light activated cured. Nevertheless, other methods are possible for curing the coating.

The handle 103, 203, 303 and base 106, 206, 306 may be constructed from a material such as a rigid or resilient material, such as a biocompatible plastic used in oral hygienic products. Tissue cleaner 109 may be preferably formed by being molded and bonded to the base 106, although other manufacturing processes could be used. For example, the tissue cleaner 109 could be attached by adhesive or other known methods to the base 106. The tissue cleaner 209, 309 may be over-molded to the base using known manufacturing methods.

Tissue cleaners 109, 209, 309, during use, may rub against the inside surfaces of the cheeks or lips, on various surfaces of the tongue, the gums, lips, and roof of the mouth and thus provide a desired massaging, stimulation and cleaning of various soft tissue surfaces within the mouth. Additionally due to mechanical interaction of the nubs, some users may sense a stimulating tingle sensation on the cheek surfaces that leads to a positive user reaction, and even enjoyment of the comfortable feel of the tissue cleaner nubs along the soft tissues surfaces in the mouth.

While a description of preferred constructions of the oral implement has been discussed, it should be understood that benefits of the invention can still be obtained with a wide variety of other constructions. For example, the material composition comprising the tissue cleaner can be incorporated with a releasable material. In one construction, a chemical substance, such as a sensate, can be released from the tissue cleaner material to invoke a biochemical sensory response in the mouth of a user. The releasable material may be released to the inside surfaces of the mouth lips, or cheeks, by way of several methods, including but not limited to abrasion, a temperature change, a change in pH, or dissolution.

In one arrangement of the oral care implement 100 and 200, the chemical substance (e.g., a sensate, medicine or the like) comprising the releasable material 107, 207 may be compounded into the elastomer and/or thermoplastic of the tissue cleaner 109, 209. In another arrangement the chemical substance may be embedded into microencapsulation form, and then compounded into the elastomer and/or thermoplastic of the tissue cleaner 109, 209. In this way, the chemical substance can be released in a generally uniform manner during use of the oral care implement. In these arrangements, the elastomeric tissue cleaner 109, 209 is provided as one homogeneous element. The chemical (e.g., sensate) will migrate outward and transfer onto the mouth soft tissues upon contact. In the arrangements of the oral care implement, the chemical substances to be released into the mouth may be pre-compounded or pre-formulated with hydrogel based, water-soluble polymers, or other biomaterial prior to final compounding into the elastomeric material forming tissue cleaner or prior to final coating of the tissue cleaner.

In one preferred construction, the chemical substances for release into the mouth can be compounded in a variety of materials, including, but not limited to thermoplastic elastomer provided by the GLS Corporation under a production designation of G6725. Nevertheless, other elastomeric compounds are possible for use with a sensate or the like.

As various changes could be made in the above methods, compositions and structures without departing from the scope of the invention, it is intended that all matter contained in this application, including all mechanisms and/or modes of interaction described above, shall be interpreted as illustrative only and not limiting in any way the scope of the appended claims.

What is claimed is:

1. An oral care implement comprising:
   an elongated handle;
   a head having a longitudinal axis, the head coupled to an end of the elongated handle and having a base constructed of a hard plastic, the base extending along, a section of the longitudinal axis;
   an integral mass of elastomeric material comprising a first portion, a second portion and a plurality of columnar tissue engaging elements extending from the first portion, the integral mass of elastomeric material attached to the base along at least a portion of the section of the longitudinal axis, the first portion of the integral mass of elastomeric material exposed from a first side of the base and the second onion of the integral mass of elastomeric material exposed from a second side of the base, the second side of the base being opposite the first side of the base; and
   a releasable material coated on the plurality of columnar tissue engaging elements, the releasable material being releasable into the mouth of a user during use.

2. The oral care implement of claim 1, wherein the first portion of the integral mass of elastomeric material supports the releasable material on its exterior.

3. The oral care implement of claim 1, wherein the integral mass of elastomeric material is covered, coated, or encased within an oral medicament.

4. The oral care implement of claim 1, wherein the releasable material comprises at least one of a breath freshener, a medicine, a sensate material, and a confectionary.

5. The oral care implement of claim 4, wherein the releasable material is dissolvable in a user's mouth.

6. The oral care implement of claim 1, wherein the releasable material forms a continuous or semi-continuous coating on a surface of the first portion of the integral mass of elastomeric material.

7. The oral care implement of claim 1, wherein the releasable material is an air-driable material, a heat assisted driable material, a heat assisted curable material, a catalyst assisted curable material, or an ultra-violet) light activated curable material.

8. The oral care implement of claim 1, wherein the handle comprises a rigid material or a resilient material.

9. The oral care implement of claim 1, wherein the integral mass of elastomeric material is molded and bonded to the base.

10. The oral care implement of claim 9, wherein the integral mass of elastomeric material is attached to the base by adhesive.

11. The oral care implement of claim 9, wherein the integral mass of elastomeric material is over-molded to the base.

12. The oral care implement of claim 1, wherein the releasable material is formulated to invoke a biochemical sensory response in a user's mouth.

13. The oral care implement of claim 1, wherein the releasable material is releasable within a user's mouth by abrasion, temperature change, pH change, dissolution, or combination thereof.

14. The oral care implement of claim 1, wherein the releasable material is compounded into the integral mass of elastomeric material.

15. The oral care implement of claim 14, wherein the releasable material is embedded into microencapsulation form and compounded into the integral mass of elastomeric material.

16. The oral care implement of claim 1, wherein the releasable material is compounded or formulated with hydrogel based, water-soluble polymers.

17. An oral care implement, comprising:
   an elongated handle;
   a head having a longitudinal axis, the head coupled to an end of the elongated handle, the head comprising a base constructed of a hard plastic and an integral mass of elastomeric material, the base extending along a section of the longitudinal axis;

the integral mass of elastomeric material attached to the base along at least a portion of the section of the longitudinal axis, the integral mass of elastomeric material comprising a first portion exposed from a first side of the base, a second portion exposed from a second side of the base and a plurality of tissue engaging elements extending from the first portion, the second side of the base being opposite the first side of the base; and a releasable material disposed on the plurality of tissue engaging elements, the releasable material being releasable into the mouth of a user during use.

18. The oral care implement of claim 17, wherein the plurality of tissue engaging elements comprise columnar elements.

19. An oral care implement, comprising:

an elongated handle;

a head having a longitudinal axis, the head coupled to the elongated handle and comprising a base and an integral mass of elastomeric material, the base constructed of a hard plastic and extending along a section of the longitudinal axis and the integral mass of elastomeric material attached to the base along at least a portion of the section of the longitudinal axis, the integral mass of elastomeric material comprising a first portion exposed on a first side of the base, a second portion exposed on a second side of the base opposite the first side of the base, and a plurality of elastomeric tissue engaging elements extending from the first side of the base; and a releasable material disposed on the plurality of elastomeric tissue engaging elements, the releasable material being releasable into the mouth of a user during use.

20. The oral care implement of claim 1 wherein the elongated handle is constructed of a rigid material.

21. The oral care implement of claim 1 wherein the elongated handle extends along a longitudinal axis form a proximal end to a distal end, the head coupled to the distal end of the elongated handle.

22. The oral care implement of claim 17 wherein the elongated handle extends along a longitudinal axis form a proximal end to a distal end, the head coupled to the distal end of the elongated handle.

23. The oral care implement of claim 19 wherein the elongated handle extends along a longitudinal axis form a proximal end to a distal end, the head coupled to the distal end of the elongated handle.

* * * * *

UNITED STATES PATENT AND TRADEMARK OFFICE
CERTIFICATE OF CORRECTION

PATENT NO. : 8,550,736 B2  
APPLICATION NO. : 12/717206  
DATED : October 8, 2013  
INVENTOR(S) : Douglas J. Hohlbein and Chi Shing Wong Page 1 of 1

It is certified that error appears in the above-identified patent and that said Letters Patent is hereby corrected as shown below:

In the claims:

Claim 1, col. 8, line 10, delete "onion" and replace it with -- portion --

Signed and Sealed this
Fifteenth Day of July, 2014

Michelle K. Lee
*Deputy Director of the United States Patent and Trademark Office*